US00PP14786P2

(12) United States Plant Patent
Uchneat

(10) Patent No.: US PP14,786 P2
(45) Date of Patent: May 18, 2004

(54) IMPATIENS PLANT NAMED 'BALPIXSANG'

(50) Latin Name: *Impatiens walleriana*
Varietal Denomination: Balpixsang

(75) Inventor: Michael S. Uchneat, St. Charles, IL (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 79 days.

(21) Appl. No.: 10/108,589

(22) Filed: Mar. 27, 2002

(51) Int. Cl.[7] ..... A01H 5/00
(52) U.S. Cl. ..... Plt./317
(58) Field of Search ..... Plt./317

*Primary Examiner*—Anne Marie Grunberg

(57) ABSTRACT

A new and distinct Impatiens plant named 'Balpixsang', characterized by its small salmon colored flowers, compact growth habit and dark green leaves.

1 Drawing Sheet

Latin name of the genus and species of plant claimed: *Impatiens walleriana.*
Variety denomination: 'Balpixsang'.

BACKGROUND OF THE INVENTION

The present invention comprises a new and distinct Impatiens plant, botanically known as *Impatiens walleriana* and hereinafter referred to by the cultivar name 'Balpixsang'.

'Balpixsang' is a product of a planned breeding program with the objective of developing Impatiens cultivars with small flowers and compact growth habits.

The female or seed parent of 'Balpixsang' was Impatiens variety 'Orange Chico' (unpatented) which has a more compact growth habit than 'Balpixsang'. The male or pollen parent of 'Balpixsang' was the proprietary Impatiens variety designated 3111-1-9 (unpatented) which has larger flowers than 'Balpixsang'. The new cultivar was discovered and selected as a single flowering plant within the progeny of the above stated cross during January 2000 in a controlled environment at Elburn, Ill. The new cultivar was designated BFP-560.

Asexual reproduction of the new cultivar has been carried out at West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits small salmon colored flowers;

(b) forms dark green foliage;

(c) exhibits a good basal branching character; and (c) exhibits a compact growth habit.

The new cultivar of the present invention can be compared to 'Fify Salmon' (U.S. Plant Pat. No. 11,559). However, in side by side comparisons, plants of the new cultivar are more vigorous, have larger leaves and have flowers that are slightly darker and more orange in color than 'Fify Salmon'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

The cultivar 'Balpixsang' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 12, 2001. The readings were taken between 2:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double polycarbonate covered greenhouse under conditions comparable to those used in commercial practice. A soilless growth medium was utilized while temperatures of approximately 68° to 75° F. (20° to 24° C.) during the day and approximately 55° to 65° F. (13° to 18° C.) during the night and light levels of 4,000 to 6,000 footcandles were maintained.

Classification:
*Botanical.*—*Impatiens walleriana* cultivar 'Balpixsang'.
Parentage:
*Female parent.*—Impatiens variety 'Orange Chico'.
*Male parent.*—Proprietary Impatiens variety designated 3111-1-9.
Propagation:
*Type cutting.*—Terminal tip.
*Time to initiate roots.*—Approximately 7 to 10 days.
*Time to develop roots.*—Approximately 21 to 30 days.
*Root description.*—Fibrous, branching.

Plant description:

*Crop time.*—Approximately 4 to 6 weeks are required to produce a finished plant from rooted cuttings.

*Habit of growth.*—Compact with good basal branching. Pinching is not required.

*Form.*—Upright and mounded.

*Height of foliage.*—A mature plant, 12 weeks after the planting of a rooted cutting, commonly measures approximately 11 cm.

*Plant spread.*—Approximately 22 cm.

*Lateral branches.*—An average of 6 branches per plant, approximately 6.3 cm in length and 4 mm in diameter, glabrous and 145B with streaks of 183D. Internode length at the middle of the branch is approximately 7 mm.

*Foliage.*—Arrangement is alternate. Leaves are single, ovate with crenate, ciliate margin, acuminate apex, attenuate base and are at an acute angle to the stem. Upper and lower surfaces are glabrous. Leaf length is approximately 3.5 cm and width is approximately 2.4 cm. The upper surface of mature foliage is 137A and the lower surface is closest to 147B. Both upper and lower surfaces have pinnate venation. Venation of upper surface is 144C and the venation of the lower surface is 144A. The petiole length is approximately 1.9 cm, the diameter is approximately 2 mm and the color is closest to 144D with streaks of 59C.

Flowering description:

*Flowering habit.*—Freely flowering.

*Natural flowering season.*—Year round in greenhouse environment and from spring through fall in outdoor garden.

Flower, description:

*Type.*—Single and persistent.

*Size.*—Diameter is approximately 2.4 cm.

*Aspect.*—Flat.

*Corolla.*—Five petals with entire undulate margin. Lateral and lower petals are fused at their bases. Lateral petals overlap lower petals and lower petals overlap each other. Upper petal has cuspidate apex, lateral petals have rounded apex and lower petals have emarginate apex. Upper petal has flat base. The base of the lateral and lower petals is attenuate. All petals have smooth texture. Upper petal length is approximately 1.1 cm and width at widest point is 1.7 cm. Lateral and lower petal length is approximately 1.7 cm and width at widest point is approximately 9 mm. Color of upper surface of upper and lateral petals is between 41A and 41B. Color of upper surface of lower petals is between 41A and 41B with area at base of 59B forming an "eye". Color of lower surface of all petals is 43D. Petal color fades to between 72A and 72B with age.

*Peduncle.*—Glabrous, at an acute angle to the stem, approximately 1.4 cm in length and 1 mm in diameter. Peduncle color is 144D.

*Flower bud.*—Ovate, approximately 9 mm in length and 6 mm in diameter at first color. Bud color is 39A.

*Sepals.*—Three. Lateral sepals are approximately 3 mm in length and 1 mm in width with acuminate apex. Lower sepal is modified into spur.

*Spur.*—Sharply curved, 2.8 cm in length and 63C.

*Reproductive organs.*—Five stamens, 3 mm in length. Anthers are fused around pistil and color is 58A. Pollen has not been observed. Pistil length is 3 mm. Style length is <1 mm and color is 59B. Stigma length is <1 mm and color is 59A. Ovary is 2 mm in length and 143C in color.

Seed production: Seed production has not been observed.

Disease resistance: Resistance to pathogens has not been observed.

Hardiness zone: 'Balpixsang' is hardy in zones nine (9) and above.

I claim:

1. A new and distinct cultivar of Impatiens plant named 'Balpixsang' substantially as herein shown and described, which:

(a) exhibits small salmon colored flowers;

(b) dark green foliage;

(c) a compact growth habit; and (d) a good basal branching character.

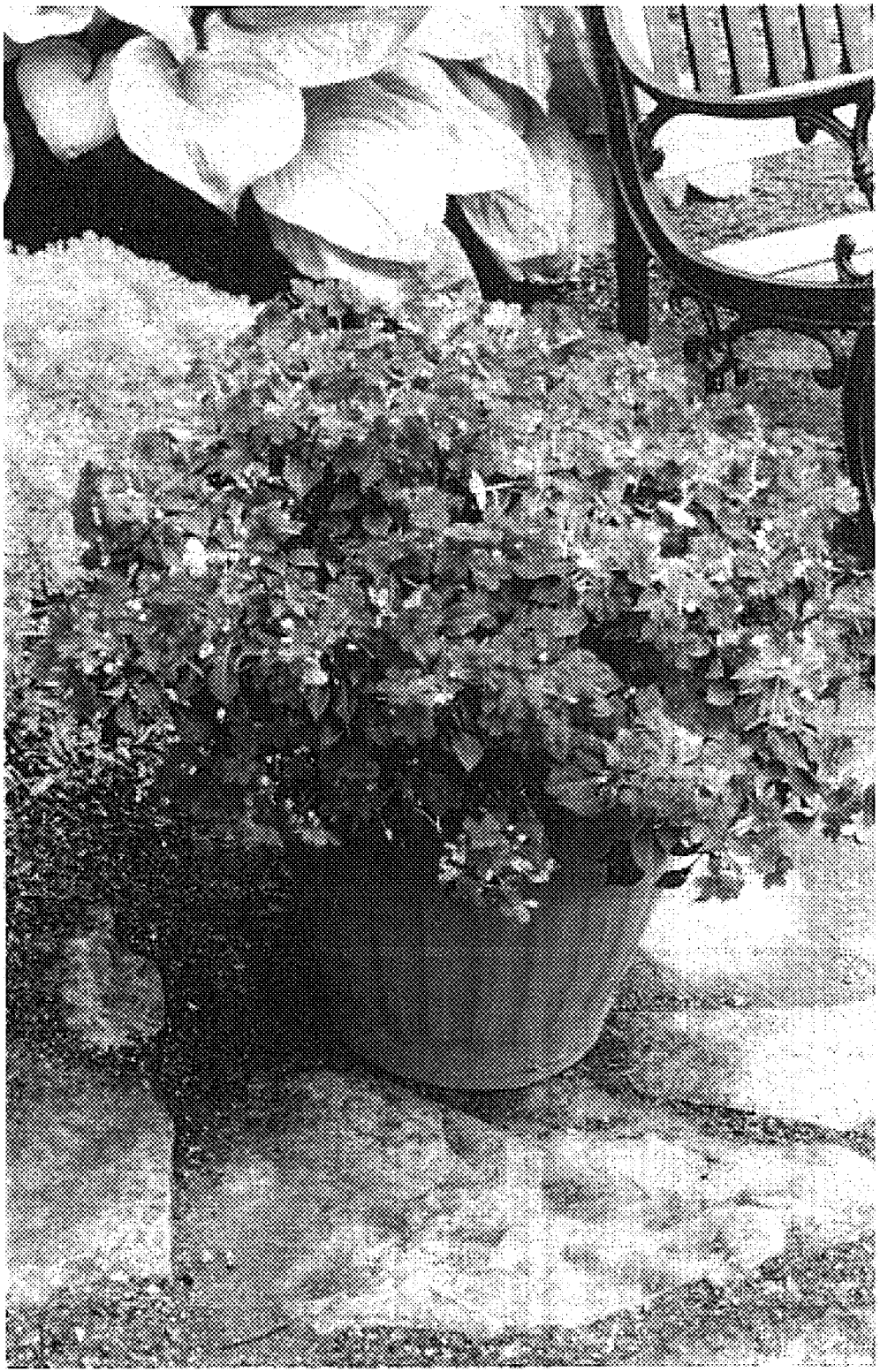

* * * * *